US006632640B1

(12) United States Patent
Lee et al.

(10) Patent No.: US 6,632,640 B1
(45) Date of Patent: Oct. 14, 2003

(54) VACCINE AGAINST STAPHYLOCOCCUS INTOXICATION

(75) Inventors: John S. Lee, Hagerstown, MD (US); Peter Pushko, Frederick, MD (US); Jonathan F. Smith, Sabillasville, MD (US); Robert G. Ulrich, Frederick, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/350,755

(22) Filed: Jul. 9, 1999

Related U.S. Application Data
(60) Provisional application No. 60/092,416, filed on Jul. 10, 1998.

(51) Int. Cl.$^7$ .................. C12N 15/09; C12N 15/00; C12N 1/20; C12P 21/04; C07H 21/04
(52) U.S. Cl. .................. 435/69.3; 435/69.1; 435/320.1; 435/325; 435/252.3; 435/252.33; 435/71.1; 435/71.3; 536/23.1; 536/23.5; 536/23.7
(58) Field of Search .................. 536/23.1, 23.5, 536/23.7; 435/69.1, 69.3, 320.1, 325, 252.3, 252.33, 71.1, 71.3

(56) References Cited

U.S. PATENT DOCUMENTS

| | | | |
|---|---|---|---|
| 5,705,151 A | * 1/1998 | Dow et al. .................. 424/450 |
| 5,789,245 A | * 8/1998 | Dubensky et al. | |
| 5,792,462 A | * 8/1998 | Johnston et al. | |
| 5,935,568 A | * 8/1999 | Dow et al. | |
| 6,015,686 A | * 1/2000 | Dubensky et al. | |
| 6,075,119 A | * 6/2000 | Bannan et al. ............ 424/130.1 |
| 6,156,558 A | * 12/2000 | Johnston et al. ......... 435/235.1 |
| 6,261,570 B1 | * 7/2001 | Parker et al. | |
| 6,296,854 B1 | * 10/2001 | Pushko et al. | |
| 6,399,332 B1 | * 6/2002 | Ulrich et al. | |

FOREIGN PATENT DOCUMENTS

| | | | |
|---|---|---|---|
| WO | WO 93/14634 | * | 8/1993 |
| WO | WO 95/07994 | | 3/1995 |
| WO | WO 96/37616 | | 11/1996 |
| WO | WO 97/31114 | * | 8/1997 |
| WO | WO 00/02523 | * | 1/2000 |
| WO | WO 00/09154 | * | 2/2000 |

OTHER PUBLICATIONS

Ulrich, FEMS Immunology and Medical Microbiology, 2000, 27:1–7.*
Lee et al, Infection and Immunity, 2001, 69/9:5709–5715.*
Kodama et al, Cancer Immunol. Immunother., 2001, 50:539–548.*
Krauss et al, J. Hematotherapy 6:41–51, 1997.*
Borst et al, Infection & Immunity 61/12:5421–5425, 1993.*
Betley et al. J. Bacterol. 170/1: 34–41, 1988.*
Gildöf et al. Blood 89/6: 2089–2097, 1997.*
Metzroth et al, Infection & Immunity 61/6:2445–52, 1993.*
Ranelli et al, PNAS, 82:5850–5854, 1985.*
Dohlsten et al PNAS 91:8945–8949, 1994.*
Buelow et al, J. Immunol. 14/1: 1–6, 1992.*
Devos et al, Nucleic Acid Research 10/8:2487–501, 1982.*
Renaud et al, Epidemology & Infection 112/3:501–511, 1994.*
Woody et al, J. Infectious Disease 177:1013–1022, 1998.*
Mahana et al, Infection & Immunity, 63/8: 2826–2832, 1995.*
Harris et al, Infection and Immunity, May 1993, 61/5:2059–2068.*
Couch et al, J. Bacteriology, Jul. 1988, 170/7:2954–2960.*
PCT International Search Report for PCT/US 99/15569, mailed Aug. 22, 2000, 13 pages (corresponding foreign application to US Ser. No. 09/350,755).
Bavari et al., "Superantigen Vaccines: A Comparative Study of Genetically Attenuated REceptor–Binding Mutants of Staphylococcal Enterotoxin A", Journal of Infectious Diseases, 174:338–345 (1996).
Ulrich et al., "Staphylococcal enterotoxins A and B share a common structural motif for binding class II major histocompatibiity complex molecules", Nature Structural Biology, vol. 2, No. 6, pp. 554–560, Jun. 1995.
Bavari et al., "Engineered Bacterial Superantigen Vaccines", Vaccines, vol. 96, pp. 135–141, 1996.
Pushko et al., "Replicon–Helper Systems from Attenuated Venezuelan Equine Encephalitis Virus: Expression of Heterologous Genes in Vitro and Immunization against Heterologous Pathogens in Vivo", Virology, vol. 239, pp. 389–401 (1997).
Ulrich et al., "Development of engineered vaccines effective against structurally related bacterial superantigens", Vaccine, vol. 16, No. 19, pp. 1857–1864 (1998).
Bavari and Ulrich, "Engineered bacterial superantigen vaccines", Toxicon, vol. 36, pp. 1231–1232 (Sep. 1998) (Abstract).
Nilsson et al., "Protection against *Staphylococcus aureus* sepsis by vaccination with recombinatn Syaphylcoccal Enterotoxin A devoid of superantigenicity", J. Infectious Diseases, vol. 180, Oct. 1999, pp. 1370–1373.

* cited by examiner

Primary Examiner—Nita Minnifield
(74) Attorney, Agent, or Firm—Elizabeth Arwine; Charles H. Harris

(57) ABSTRACT

Using nucleic acids encoding mutant SEA and SEB exotoxins from *Staphylococcus aureus*, compositions and methods for use in inducing an immune response which is protective against *staphylococcal aureus* intoxication in subjects is described.

9 Claims, 3 Drawing Sheets

SEQUENCE LISTING

<160> NUMBER OF SEQ ID NOS: 3

<210> SEQ ID NO 1
<211> LENGTH: 757
<212> TYPE: DNA
<213> ORGANISM: Staphyloccus aureus

<400> SEQUENCE: 1

```
atgagaaaag cgaagaaata aatgaaaaag atttgcgaaa                40
aaagtctgaa ttgcagggaa cagctttagg caatcttaaa                80
caaatctatt attacaatga aaaagctaaa actgaaaata               120
aagagagtca cgatcaattt cgacagcata ctatattgtt               160
```

-continued

```
taaaggcttt tttacagatc attcgtggta taacgattta          200
ttagtacgtt ttgattcaaa ggatattgtt gataaatata          240
aagggaaaaa agtagacttg tatggtgctt atgctggtta          280
tcaatgtgcg ggtggtacac caaacaaaac agcttgtatg          320
tatggtggtg taacgttaca tgataataat cgattgaccg          360
aagagaaaaa agtgccgatc aatttatggc tagacggtaa          400
acaaaataca gtacctttgg aaacggttaa acgaataag           440 aaaaatgtaa ctgttcagga gttggatctt caagcaagac          480
gttatttaca ggaaaaatat aatttatata actctgatgt          520
ttttgatggg aaggttcaga ggggattaat cgtgtttcat          560
acttctacag aaccttcggt taattacgat ttatttggtg          600
ctcaaggaca gtattcaaat acactattaa gaatatatag          640
agataataaa acgattaact ctgaaaacat gcatattgat          680
atatatttat atacaagtta aacatggtag ttttgaccaa          720
cgtaatgttc agattattat gaaccgagaa taatcta             757
```

<210> SEQ ID NO 2
<211> LENGTH: 801
<212> TYPE: DNA
<213> ORGANISM: Staphylococcus aureus

<400> SEQUENCE: 2

```
atgtataaga gattatttat ttcacatgta attttgatat           40
tcgcactgat attagttatt tctacaccca acgttttagc           80
agagagtcaa ccagatccta aaccagatga gttgcacaaa          120
tcgagtaaat tcactggttt gatggaaaat atgaaagttt          160
tgtatgatga taatcatgta tcagcaataa acgttaaatc          200
tatagatcaa tttcgatact ttgacttaat atattctatt          240
aaggacacta gttagggaa ttatgataat gttcgagtcg           280
aatttaaaaa caaagattta gctgataaat acaaagataa          320
atacgtagat gtgtttggag ctaatgctta ttatcaatgt          360
gcttttccta aaaaaacgaa tgatattaat tcgcatcaaa          400
ctgacaaacg aaaaacttgt atgtatggtg gtgtaactga          440
gcataatgga aaccaattag ataaatatag aagtattact          480
gttcgggtat ttgaagatgg taaaaattta ttatcttttg          520
acgtacaaac taataagaaa aaggtgactg ctcaagaatt          560
agattaccta actcgtcact atttggtgaa aaataaaaaa          600
ctctatgaat ttaacaactc gccttatgaa acgggatata          640
ttaaatttat agaaaatgag aatagctttt ggtatgacat          680
gatgcctgca ccaggagata aatttgacca atctaaatat          720
ttaatgatgt acaatgacaa taaaatggtt gattctaaag          760
atgtgaagat tgaagtttat cttacgacaa agaaaaagtg          800
```

-continued

```
a                                                                          801

<210> SEQ ID NO 3
<211> LENGTH: 723
<212> TYPE: DNA
<213> ORGANISM: Staphylococcus aureus

<400> SEQUENCE: 3
atggagagtc aaccagatcc taaaccagat gagttgcaca                                 40
aatcgagtaa attcactggt ttgatggaaa atatgaaagt                                 80
tttgtatgat gataatcatg tatcagcaat aaacgttaaa                                120
tctatagatc aatttcgata ctttgactta atatattcta                                160
ttaaggacac taagttaggg aattatgata atgttcgagt                                200
cgaatttaaa aacaaagatt tagctgataa atacaaagat                                240
aaatacgtag atgtgtttgg agctaatgct tattatcaat                                280
gtgctttttc taaaaaaacg aatgatatta attcgcatca                                320
aactgacaaa cgaaaaactt gtatgtatgg tggtgtaact                                360
gagcataatg gaaaccaatt agataaatat agaagtatta                                400
ctgttcgggt atttgaagat ggtaaaaatt tattatcttt                                440
tgacgtacaa actaataaga aaaaggtgac tgctcaagaa                                480
ttagattacc taactcgtca ctatttggtg aaaaataaaa                                520
aactctatga atttaacaac tcgccttatg aaacgggata                                560
tattaaattt atagaaaatg agaatagctt ttggtatgac                                600
atgatgcctg caccaggaga taaatttgac caatctaaat                                640
atttaatgat gtacaatgac aataaaatgg ttgattctaa                                680
agatgtgaag attgaagttt atcttacgac aaagaaaaag                                720
tga                                                                        723
```

VACCINE AGAINST STAPHYLOCOCCUS INTOXICATION

This application claims the benefit of provisional application No. 60/092,416 filed Jul. 10, 1998.

FIELD OF THE INVENTION

This invention relates to vaccines for bacterial toxins from *Staphylococcus aureus*.

INTRODUCTION

The most common cases of food poisoning are caused by the bacteria *Staphylococcus aureus*. Exotoxins produced by the organism cause gastrointestinal distress, to include diarrhea and vomiting, and can also cause toxic shock syndrome which may lead to death. These exotoxins also called enterotoxins since they typically exert their effects on the gastrointestinal tract, cause disease by binding to the major histocompatibility complex (MHC) on T-cells which results in the release of large amounts of various cytokines. This cytokine release has been postulated to mediate the many toxic effects of the *S. aureus* exotoxins. There are at least eight antigenically distinct exotoxins (labeled SEA, SEB, SEC1, SEC2, SEC3, SED, SEE, and SEG) produced by *S. aureus*. Presently, there is no approved/licensed SEA or SEB vaccine. Treatment for *Staphylococcus aureus* infections is becoming more difficult since the organism has become resistant to most antibiotics.

Therefore, there is a need for an efficacious vaccine protective against *Staphylococcus aureus* intoxication.

SUMMARY OF THE INVENTION

The present invention satisfies the need discussed above. The present invention relates to a method and composition for use in inducing an immune response which is protective against intoxication with *Staphylococcus aureus*.

In this application is described a vaccine strategy where a gene coding for a protein of interest is cloned in a VEE virus vector in place of the VEE virus structural genes; the result is a self-replicating RNA molecule, a replicon, that encodes its own replicase and transcriptase functions, and in addition makes abundant quantities of mRNA encoding the foreign protein. When replicon RNA is transfected into eukaryotic cells along with two helper RNAs that express the VEE structural proteins (glycoproteins and nucleocapsid), the replicon RNA is packaged into VEE virus-like particles by the VEE virus structural proteins, which are provided in trans. Since the helper RNAs lack packaging signals necessary for further propagation, the resulting VEE replicon particles (VRPs) which are produced are infectious for one cycle but are defective thereafter. Upon infection of an individual cell with a VRP, an abortive infection occurs in which the infected cell produces the protein of interest in abundance, is ultimately killed by the infection, but does not produce any viral progeny (Pushko et al., 1997, *Virology* 239, 389–401).

Genes encoding a mutant SEA (mSEA) exotoxin and a mutant SEB (mSEB) exotoxin were each inserted into the VEE replicon vaccine vector (FIG. 1). The mutant gene product is unable to bind to the MHC on T-cells (Bavari, et al., 1996, *Vaccines* 96, 135–141). Evaluation of the mSEA-replicon and mSEB-replicon in vitro have shown high level expression of both bacterial proteins. Balb/c mice immunized with the mSEB-replicon produced high specific antibody titers and were protected when challenged intraperitoneally with wild type SEB.

Therefore, it is one object of the present invention to provide a VEE virus replicon vector comprising a VEE virus replicon and a DNA fragment encoding a mutant SEA exotoxin or a mutant SEB exotoxin.

It is another object of the present invention to provide a self replicating RNA comprising the VEE virus replicon and any of the SEA or SEB fragments described above.

It is another object of the present invention to provide infectious VEE virus replicon particles produced from the VEE virus replicon RNA described above.

It is further an object of the invention to provide an immunological composition for the protection of mammals against *Staphylococcus aureus* intoxication comprising VEE virus replicon particles containing any of the *Staphylococcus aureus* fragments described above or a combination of different VEE virus replicons each having a different *Staphylococcus aureus* fragment.

BRIEF DESCRIPTION OF THE DRAWINGS

These and other features, aspects, and advantages of the present invention will become better understood with reference to the following description and appended claims, and accompanying drawings where:

Figure 1:
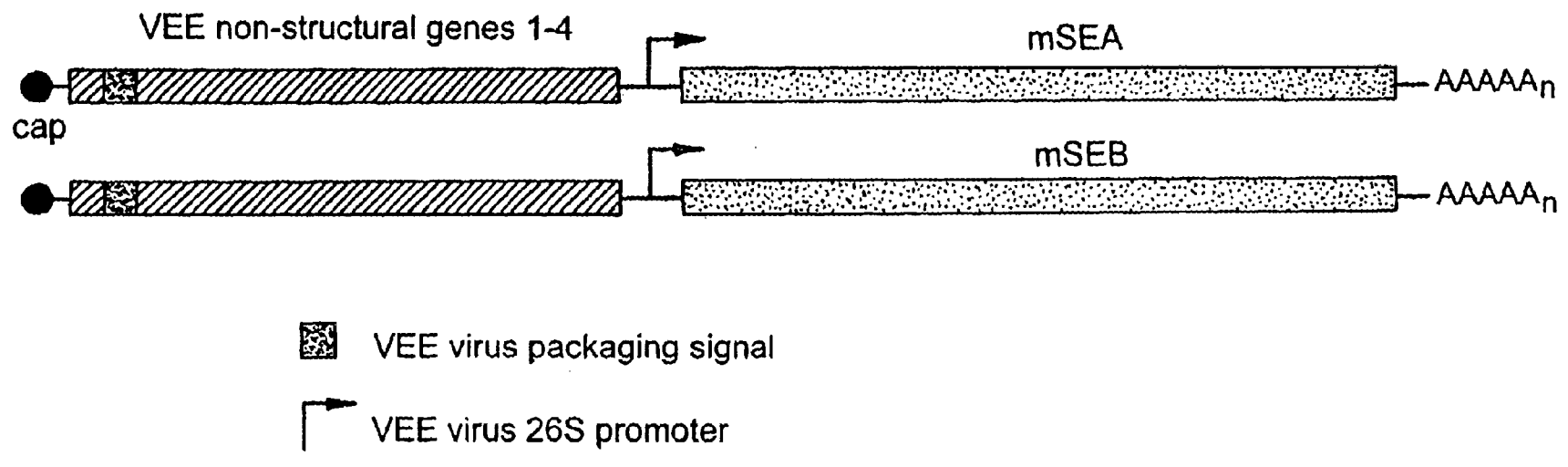

FIG. 1. Diagram of the mSEA and mSEB replicon constructs. The replicons are similar to the full-length VEE RNA except that the open reading frame encoding the VEE structural proteins was replaced with either the mSEA or mSEB genes.

FIG. 2. Western blot of BHK cell lysates showing expression of mSEA or mSEB (containing a 5' prokaryotic secretory signal) from recombinant VEE replicons. a) transfected cell lysate; b) infected cell lysate; c) commercially available product.

DETAILED DESCRIPTION

Figure 3:
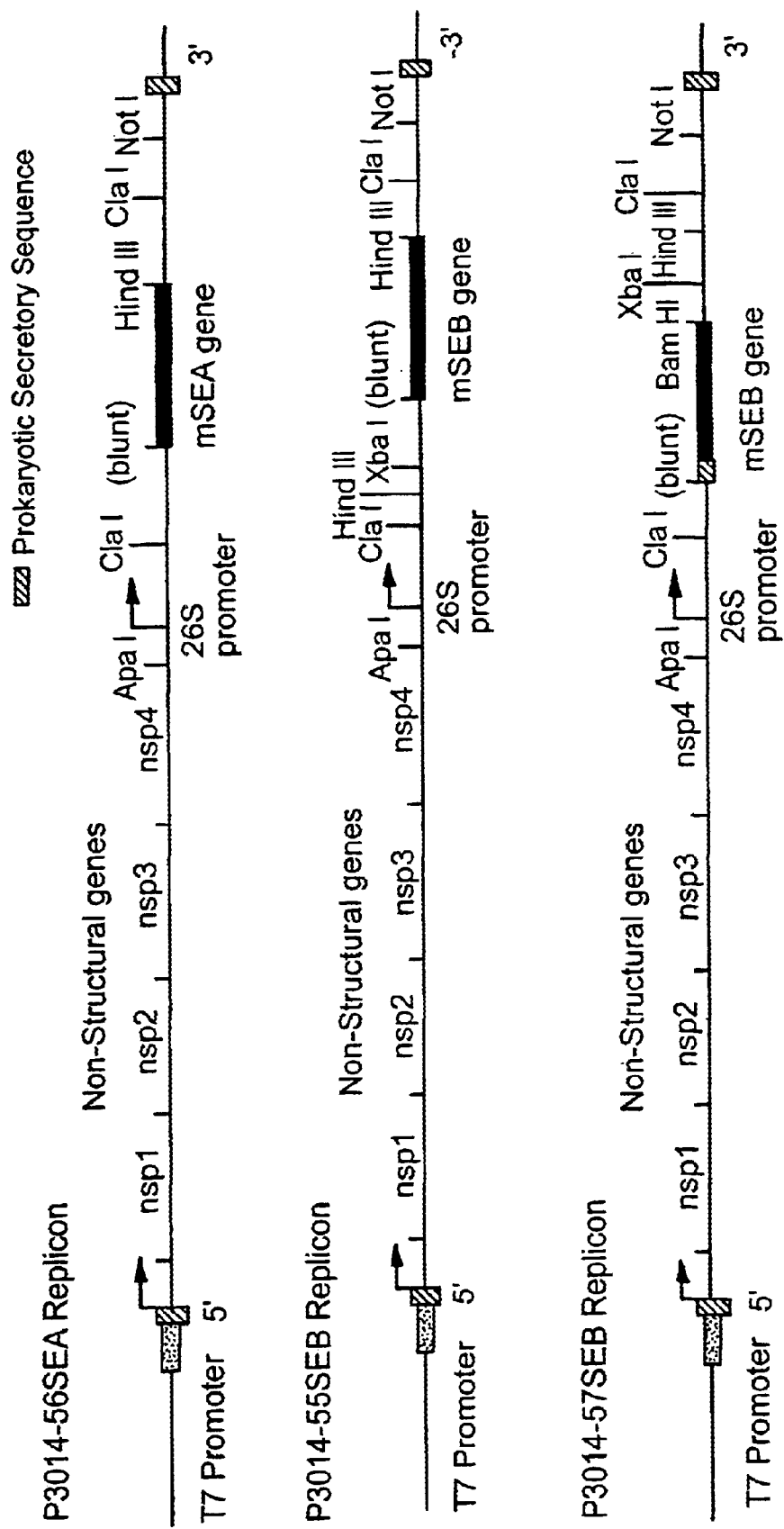
FIG. 3. Schematic diagram of replicon constructs containing mutant SEA or mutant SEB DNA fragments.

In the description that follows, a number of terms used in recombinant DNA, virology and immunology are extensively utilized. In order to provide a clearer and consistent understanding of the specification and claims, including the scope to be given such terms, the following definitions are provided.

Replicon

A replicon is equivalent to a full length virus from which all of the viral structural proteins have been deleted. A multiple cloning site can be cloned into the site previously occupied by the structural protein genes. Virtually any heterologous gene may be cloned into this cloning site.

Transcription of the RNA from the replicon yields an RNA capable of initiating infection of the cell identically to that seen with the full-length infectious virus clone. However, in lieu of the viral structural proteins, the heterologous antigen is expressed. This system does not yield any progeny, virus particles because there are no viral structural proteins available to package the RNA into particles.

Particles which appear structurally identical to virus particles can be produced by supplying structural proteins for packaging of the replicon RNA in trans. This is typically done with two helpers also called defective helper RNAs. One helper consists of a full length infectious clone from which the nonstructural protein genes and the glycoprotein genes are deleted. The helper retains only the terminal nucleotide sequences, the promoter for subgenomic mRNA transcription and the sequences for the viral nucleocapsid protein. The second helper is identical to the first except that the nucleocapsid gene is deleted and only the glycoprotein genes are retained. The helper RNA's are transcribed in vitro and co-transfected with replicon RNA. Because the replicon RNA retains the sequences for packaging by the nucleocapsid protein, and because the helpers lack these sequences, only the replicon RNA is packaged by the viral structural proteins and released from the cell. The particles can then be inoculated into animals similar to parent virus. The replicon particles will initiate only a single round of replication because the helpers are absent, they produce no progeny virus particles, and express only the viral nonstructural proteins and the product of the heterologous gene cloned in place to the structural proteins.

The VEE virus replicon is a genetically reorganized version of the VEE virus genome in which the structural proteins genes are replaced with a gene from an immunogen of interest, in this invention, the staphylococcal proteins. The result is a self replicating RNA (replicon) that can be packaged into infectious particles using defective helper RNAs that encode the glycoprotein and capsid proteins of the VEE virus.

Subject

Includes both human, animal, e.g., horse, cattle, donkey, monkey, pig, dog, guinea pig, mouse, hamster, avian e.g., chicken; pheasant or turkey, fish and other marine animals, and insects such as mosquito.

In one embodiment, the present invention relates to a recombinant DNA molecule that includes a VEE replicon and a DNA sequence encoding mutant *Staphylococcus aureus* A and B exotoxins. The sequence mSEA and mSEB has been determined and is presented in SEQ ID NO:1 and SEQ ID NO:2, respectively. In addition, isolated nucleic acid molecules of the invention include DNA molecules which comprise a sequence substantially different from those described above but which, due to the degeneracy of the genetic code, still encode the *Staphylococcus aureus* proteins described. Of course, the genetic code and species-specific codon preferences are well known in the art. Thus, it would be routine for one skilled in the art to generate the degenerate variants described above, for instance, to optimize codon expression for a particular host (e.g., change codons in the human mRNA to those preferred by a bacterial host such as *E.coli*).

Nucleic acid molecules of the present invention may be in the form of RNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the antisense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

The present invention is further directed to nucleic acid molecules comprising portions or fragments of the nucleotide sequences described herein. Fragments include portions of the nucleotide sequences of at least 10 contiguous nucleotides in length selected from any two integers, one of which representing a 5' nucleotide position and a second of which representing a 3' nucleotide position, where the first nucleotide for each nucleotide sequence is position 1. That is, every combination of a 5' and 3' nucleotide position that a fragment at least 10 contiguous nucleotide bases in length or any integer between 10 and the length of an entire nucleotide sequence minus 1.

The present invention further relates to variants of the nucleic acid molecules of the present invention, which encode portions, analogs or derivatives of the *Staphylococcus aureus* polypeptides described above. Variants may occur naturally, such as a natural allelic variant. By an "allelic variant" is intended one of several alternate forms of a gene occupying a given locus of a chromosome of an organism. Non-naturally occuring variants may be produced by known mutagenesis techniques. Such variants include those produced by nucleotide substitution, deletion or addition of one or more nucleotides in the coding or noncoding regions or both. Alterations in the coding regions may produce conservative or nonconservative amino acid substitutions, deletions, or additions. Especially preferred among these are silent substitutions, additions, and deletions which do not alter the properties and activities of the *Staphylococcus aureus* polypeptides disclosed herein or portions thereof. Also preferred in this regard are conservative substitutions.

In another embodiment, the present invention relates to a recombinant DNA molecule that includes a vector and a DNA sequence as described above. The vector can take the form of a plasmid, phage, cosmid, YAC, eukaryotic expression vector such as a DNA vector, *Pichia pastoris,* or a virus vector such as for example, baculovirus vectors, retroviral vectors or adenoviral vectors, and others known in the art. The cloned gene may optionally be placed under the control of (i.e., operably linked to) certain control sequences such as promoter sequences, or sequences which may be inducible and/or cell type-specific. Suitable promoters will be known to a person with ordinary skill in the art. The expression construct will further contain sites for transcription initiation, termination and, in the transcribed region, a ribosome binding site for translation. When the DNA sequences described above are in a replicon expression system, such as the VEE replicon described above, the proteins can be expressed in vivo. The DNA sequence for any of the *Staphylococcus aureus* proteins described above can be cloned into the multiple cloning site of a replicon such that transcription of the RNA from the replicon yields an infectious RNA containing the *Staphylococcus aureus* protein or proteins of interest. Use of helper RNA containing sequences necessary for encapsulation of the viral transcript will result in the production of viral particles containing replicon RNA which are able to infect a host and initiate a single round of replication resulting in the expression of the *Staphylococcus aureus* proteins. Such replicon constructs include those specified in Table 1.

TABLE 1

| Plasmid Name | Replicon Serotype | expresses |
|---|---|---|
| p3014-56SEA | SEA | mutated SEA |
| p3014-55SEB | SEB | mutated SEB |

TABLE 1-continued

| | Replicon | |
| --- | --- | --- |
| Plasmid Name | Serotype | expresses |
| p3014-57SEB | SEB | prokaryotic secretory sequence-mutated SEB |

These three plasmids were deposited with the American Type Culture Collection, located at 10801 University Blvd., Manassas, Va. 20110-2209, USA, on Feb. 1, 2002, under the conditions of the Budapest Treaty. Plasmid p3014-56SEA was assigned the deposit designation PTA-4033; plasmid p3014-55SEB was assigned the deposit designation PTA-4032; and plasmid p3014-57SEB was assigned the deposit designation PTA4034.

In another embodiment, the present invention relates to RNA molecules resulting from the transcription of the constructs described above. The RNA molecules can be prepared by in vitro transcription using methods known in the art and described in the Examples below. Alternatively, the RNA molecules can be produced by transcription of the constructs in vivo, and isolating the RNA. These and other methods for obtaining RNA transcripts of the constructs are known in the art. Please see *Current Protocols in Molecular Biology.* Frederick M. Ausubel et al. (eds.), John Wiley and Sons, Inc. The RNA molecules can be used, for example, as a nucleic acid vaccine, or to transfect cells along with RNA from helper plasmids, one of which expresses VEE glycoproteins and the other VEE capsid proteins, as described above, in order to obtain replicon particles.

Introduction of the construct into the host cell can be effected by calcium phosphate transfection, electroporation, infection, and other methods known in the art and described in standard laboratory manuals such as *Current Protocols in Molecular Biology,* Ausubel, F. M. et al. (Eds), Wiley & Sons, Inc. All documents cited herein supra and infra are hereby incorporated in their entirety by referece thereto.

In a further embodiment, the present invention relates to host cells stably transformed or transfected with the above-described recombinant DNA constructs. The host cell can be prokaryotic (for example, bacterial), lower eukaryotic (for example, yeast or insect) or higher eukaryotic (for example, all mammals, including but not limited to rat and human). Both prokaryotic and eukaryotic host cells may be used for expression of desired coding sequences when appropriate control sequences which are compatible with the designated host are used. Among prokaryotic hosts, *E. coli* is most frequently used. Expression control sequences for prokaryotes include promoters, optionally containing operator portions, and ribosome binding sites. Transfer vectors compatible with prokaryotic hosts are commonly derived from, for example, pBR322, a plasmid containing operons conferring ampicillin and tetracycline resistance, and the various pUC vectors, which also contain sequences conferring antibiotic resistance markers. These markers may be used to obtain successful transformants by selection. Please see e.g., Maniatis, Fitsch and Sambrook, *Molecular Cloning: A Laboratory Manual* (1982) or *DNA Cloning,* Volumes I and II (D. N. Glover ed. 1985) for general cloning methods. The DNA sequence can be present in the vector operably linked to a sequence encoding an IgG molecule, an adjuvant, a carrier, or an agent for aid in purification of protein of the invention, such as glutathione S-transferase. The recombinant molecule can be suitable for transfecting eukaryotic cells, for example, mammalian cells and yeast cells in culture systems. *Saccharomyces cerevisiae, Saccharomyces carlsbergensis,* and *Pichia pastoris* are the most commonly used yeast hosts, and are convenient fungal hosts. Control sequences for yeast vectors are known in the art. Mammalian cell lines available as hosts for expression are known in the art and include many immortalized cell lines available from the American Type Culture Collection (ATCC), such as baby hamster kidney (BHK) cells, MRC-5 cells, and vero cells, to name a few. Suitable promoters are also known in the art and include viral promoters such as that from SV40, Rous sarcoma virus (RSV), adenovirus (ADV), bovine papilloma virus (BPV), and cytomegalovirus (CMV). Mammalian cells may also require terminator sequences and poly A addition sequences; enhancer sequences which increase expression may also be included, and sequences which cause amplification of the gene may also be desirable. These sequences are known in the art. The transformed or transfected host cells can be used as a source of DNA sequences described above. When the recombinant molecule takes the form of an expression system, the transformed or transfected cells can be used as a source of the protein described below.

A polypeptide or amino acid sequence derived from the amino acid sequences mentioned above, refers to a polypeptide having an amino acid sequence identical to that of a polypeptide encoded in the sequence, or a portion thereof wherein the portion consists of at least 2–5 amino acids, and more preferably at least 8–10 amino acids, and even more preferably at least 11–15 amino acids, or which is immunologically identifiable with a polypeptide encoded in the sequence.

A recombinant or derived polypeptide is not necessarily translated from a designated nucleic acid sequence; it may be generated in any manner, including for example, chemical synthesis, or expression of a recombinant expression system. In addition the polypeptide can be fused to other proteins or polypeptides which increase its antigenicity, such as adjuvants for example.

The recombinant or fusion protein can be used as a vaccine for immunity against staphycococcal intoxication or as a diagnostic tool for detection of staphylococcus exotoxin. The transformed host cells can be used to analyze the effectiveness of drugs and agents which inhibit *Staphylococcus aureus* exotoxins or release of the exotoxins, such as host proteins or chemically derived agents or other proteins which may interact with *Staphylococcus aureus* proteins of the present invention to inhibit its function. A method for testing the effectiveness of an anti-staphylococcus drug or agent can be, for example, mixing the antisera, drug, or agent with the enterotoxins and then injecting the mixture into a naïve mouse. If the mouse survives, then the drug or agent is effective at preventing intoxication. In other words, passive transfer of sera/antibodies is used to evaluate whether or not an agent can be neutralized by antibodies only (a humoral immune response), or if a cytotoxic T cell respone is necessary (a cellular immune response).

In another embodiment, the present invention relates to a vaccine against staphylococcal intoxication comprising one or more replicon particles derived from one or more replicons encoding one or more *Staphylococcus aureus* proteins or polypeptides as described above. The present invention relates to a method for providing immunity against staphylococcal intoxication said method comprising administering one or more replicon particles containing any combination of the *Staphylococcus aureus* proteins to a subject such that a protective immune reaction is generated. In addition, the replicon can optionally contain a second or more antigens for which protection is desired since the replicon vector can accomodate up to 5 kb of foreign sequence. The additional antigens can induce additional and different desired immunity, or can be used for increasing the immunogenicity of the first antigen. Other uses and other antigens will be evident to a person with ordinary skill in the art upon reading the present application. Serological cross-protection has been found between A and E, and B and C exotoxins (Spero and Metzger, 1981, *Methods in Enzymology* 78, 331–336). It is therefore possible that immunization with one serotype will provide protection from intoxication with another serotype.

Vaccine formulations of the present invention comprise an immunogenic amount of a replicon particle, resulting from one of the replicon constructs described above, or a combination of replicon particles as a multivalent vaccine, in combination with a pharmaceutically acceptable carrier. An "immunogenic amount" is an amount of the replicon particles sufficient to evoke an immune response in the subject to which the vaccine is administered. An amount of from about $10^2$ to $10^7$ per dose is suitable, more or less can be used depending upon the age and species of the subject being treated. Exemplary pharmaceutically acceptable carriers include, but are not limited to, sterile pyrogen-free water and sterile pyrogen-free physiological saline solution.

Administration of the replicon particles disclosed herein may be carried out by any suitable means, including both parenteral injection (such as intraperitoneal, subcutaneous, or intramuscular injection), by in ovo injection in birds, orally and by topical application of the virus (typically carried in the pharmaceutical formulation) to an airway surface. Topical application of the virus to an airway surface can be carried out by intranasal administration (e.g. by use of dropper, swab, or inhaler which deposits a pharmaceutical formulation intranasally). Topical application of the virus to an airway surface can also be carried out by inhalation administration, such as by creating respirable particles of a pharmaceutical formulation (including both solid particles and liquid particles) containing the replicon as an aerosol suspension, and then causing the subject to inhale the respirable particles. Methods and apparatus for administering respirable particles of pharmaceutical formulations are well known, and any conventional technique can be employed. An "immunogenic amount" is an amount of the replicon particles sufficient to evoke an immune response in the subject to which the vaccine is administered.

When the replicon RNA or DNA is used as a vaccine, the replicon RNA or DNA can be administered directly using techniques such as delivery on gold beads (gene gun), delivery by liposomes, or direct injection, among other methods known to people in the art. Any one or more constructs or replicating RNA described above can be use in any combination effective to elicit an immunogenic response in a subject. Generally, the nucleic acid vaccine administered may be in an amount of about 1–5 ug of nucleic acid per dose and will depend on the subject to be treated, capacity of the subject's immune system to develop the desired immune response, and the degree of protection desired. Precise amounts of the vaccine to be administered may depend on the judgement of the practitioner and may be peculiar to each subject and antigen.

The vaccine may be given in a single dose schedule, preferably a multiple dose schedule in which a primary course of vaccination may be with 1–10 separate doses, followed by other doses given at subsequent time intervals required to maintain and or reinforce the immune response, for example, at 1–4 months for a second dose, and if needed, a subsequent dose(s) after several months. Examples of suitable immunization schedules include: (i) 0, 1 months and 6 months, (ii) 0, 7 days and 1 month, (iii) 0 and 1 month, (iv) 0 and 6 months, or other schedules sufficient to elicit the desired immune responses expected to confer protective immunity, or reduce disease symptoms, or reduce severity of disease.

The following MATERIALS AND METHODS were used in the examples that follow.

The Venezuelan equine encephalitis (VEE) virus replicon vaccine vector system was used for the mutagenized, non-toxic staphylococcal enterotoxin A (mSEA) or B (mSEB) protein. This system is composed of a self-replicating RNA expression vector (replicon) containing all of the VEE virus non-structural genes and a heterologous gene (e.g. mSEA, or mSEB) in place of the VEE structural genes. Cotransfection (by electroporation) of cells in vitro with a replicon and two helper RNA molecules, the latter encoding all of the VEE structural proteins, results in the production of propagation-deficient VEE replicon particles (VRPs). The mSEA and mSEB-replicons were efficiently packaged into VRPs using the double helper system. Stock solution's contained about $10^8$ iu of purified VRP per milliliter.

Replicon p3014-56SEA was cloned as follows: The plasmid pETA489270C containing the mutant SEA gene (SEQ ID NO:1) was linearized using Nde I and the overhanging ends were filled in using DNA polymerase I. Next the plasmid was cut with Hind III which released the SEA gene. The gene was ligated into the KS2 shutle, which was previously linearized with EcoR I, filled in using DNA polymerase I, and then cut with Hind III. The gene was cut out of the shuttle using Apa I and Not I and then ligated into the replicon pVR2 (Drawing sheet 1, U.S. Pat. No. 5,792, 462 Johnston et al.).

Replicon p3014-55SEB was cloned as follows: The plasmid pETASEB3 containing a mutant SEB gene without a secretory signal (SEQ ID NO:3) was linearized using Nde I and then the overhanging ends were filled in using DNA polymerase I. Next the plasmid was cut with EcoR I which released the SEB gene. The gene was ligated into the KS1 shutle, which was previously linearized with BamH I, filled in using DNA polymerase I, and then cut with EcoR I. The gene was cut out of the shuttle using Apa I and Not I and then ligated into the replicon pVR2.

Replicon p3014-57SEB was cloned as follows: The plasmid pETB899445P containing a mutant SEB gene (SEQ ID NO:2) was linearized using Nde I and then the overhanging ends were filled in using DNA polymerase I. Next, the plasmid was cut with BamH I which released the SEB gene containing a prokaryotic secretory signal. The gene was ligated into the KS2 shutle, which was previously linearized-with EcoR I, filled in using DNA polymerase I, and then cut with BamH I. The gene was cut out of the shuttle using Apa I and Not I and then ligated into the replicon pVR2.

Figure 2:
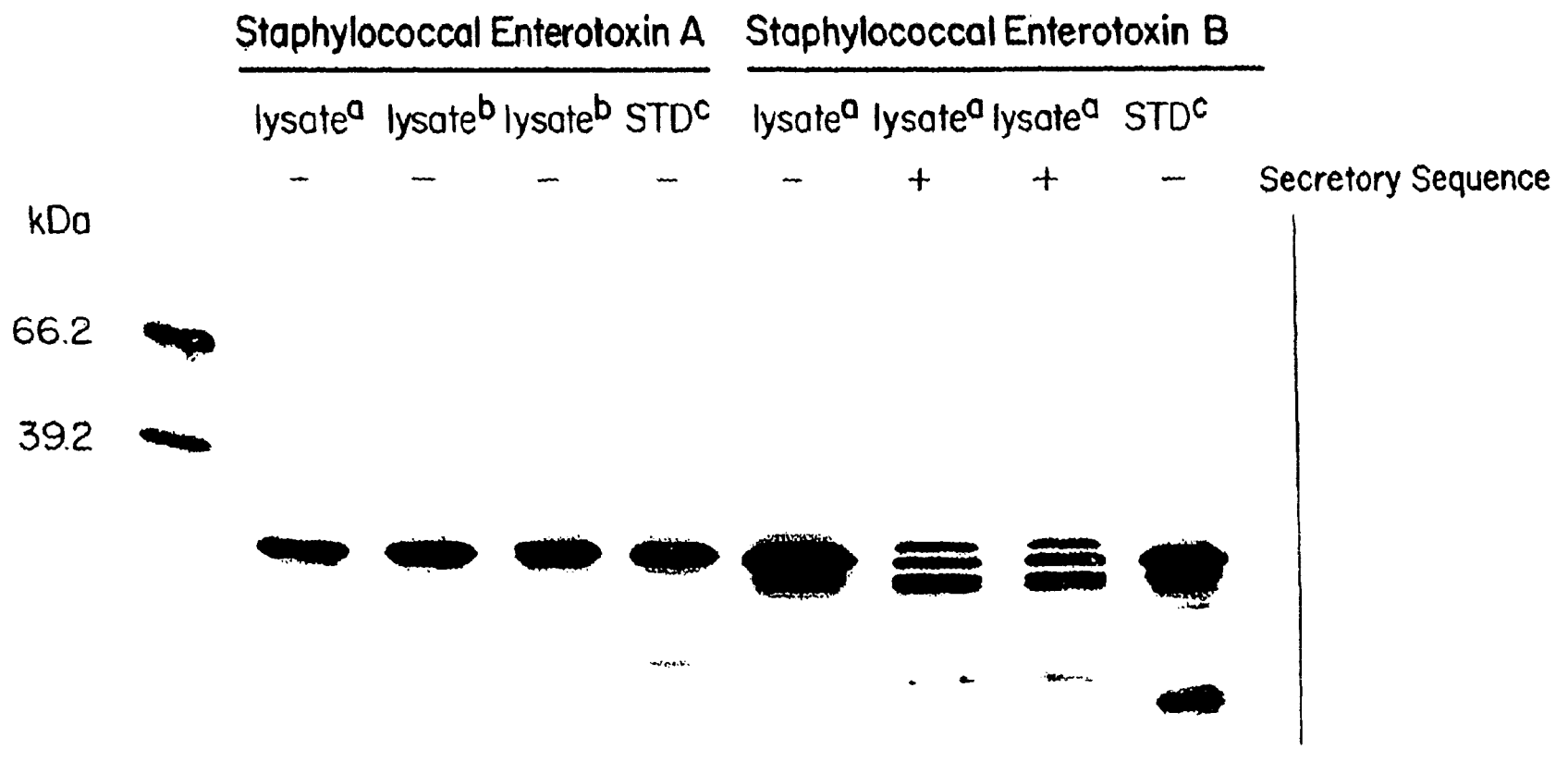

VRPs containing replicons encoding the above bacterial genes were purified from BHK cell culture supernatants by ultracentrifugation through a discontinuous sucrose gradient (20%) to remove cell culture impurities. After reconstituting the pelleted VRP in phosphate buffered saline, the VRPs were stored at –70 degrees centigrade and showed no loss in concentration or activity. Cells infected with replicons encoding mutagenized SEA or SEB expressed high levels of these proteins when analyzed by western blot (FIG. 2). VRPs were tittered using an immunofluorescence assay in cultures of BHK cells and expressed as focus forming units (FFU). One FFU is equivalent to one infectious unit. VRP preparations were monitored for the generation of replication competent VEE virus using a standard plaque forming assay. No plaque forming units (PFU) were found in any of the replicon preparations.

For the enzyme-linked immunosorbent assay (ELISA), microtiter plates were coated with antigen (0.5 ug/ml) in PBS and allowed to absorb overnight at 4° C. Four fold serum dilutions in blocking buffer were applied to the plates and incubated at 37° C. for 1 hour. After washing, an anti-mouse secondary antibody (HRP conjugated) was added to the plate and incubated for an additional hour at 37° C. After washing, bound antibody was detected colormetrically using ABTS as a substrate.

BALB/c mice were inoculated subcutaneously with $10^5$ to $10^7$ FFU of VRP containing the mSEB-replicon two or three times at 28 day intervals. Control mice were inoculated with 10 ug of mSEB absorbed to 0.28% alhydrogel (EM Sergeant Pulp and Chemical Co. Inc., Clifton, N.J.) or $10^7$ infectious units of the Lassa N replicon subcutaneously two or three times at 28 day intervals. The mice were intraperitoneally challenged 28 days after the last inoculation with wild type SEB (1.25 ug or approximately 5 $LD_{50}$) and then four hours later with LPS (40 ug).

EXAMPLE 1

Staphylococcal Enterotoxin A and B Studies

Cells infected with replicons encoding either mutagenized SEA or SEB expressed high levels of these proteins as demonstrated by western blot. VEE replicons expressing the mutated SEA or SEB genes produced proteins that comigrated on gels with authentic toxin protein and reacted efficiently with antibodies raised to the authentic proteins (FIG. 2). The mSEA and mSEB-replicons were efficiently packaged into VRPs using the double helper system. Stock solutions contained about $10^8$ iu of purified VRP per milliliter. No replication competent virus was detected in any of the preparations. The VRPs containing the SEA-replicon and SEB-replicon were characterized using an immunofluorescence assay and shown to produce immunoreactive proteins in eukaryotic cell cultures. The results of the animal studies showed that the SEB-replicon could immunize and protect mice from a lethal challenge of wild type SEB. Table 2 shows survival and ELISA results for mice inoculated 2 or 3 times with $10^5$, $10^6$, or $10^7$ FFU of VRP containing the mSEB-replicon. The mSEB-replicon protected the mice as well as the previously reported mutagenized mSEB/alum vaccine (Bavari, 1996, supra). The mSEB-replicon stimulated a dose dependent antibody response in BALB/c mice with protection correlating directly with serum ELISA titers to SEB.

TABLE 2

SEB replicon protects Balb/c mice from wild type SEB Challenge

| inoculum | dose[1] | No. of inoculations[2] | Survived total | GMT |
| --- | --- | --- | --- | --- |
| SEB/alum | 10 μg | 2 | 10/10 | 1882027 |
| SEB/alum | 10 μg | 3 | 15/19 | n.d. |
| Lassa N Rep | $10^7$ | 2 | 0/10 | 93 |
| Lassa N Rep | $10^7$ | 3 | 0/5 | n.d. |
| SEB Rep | $10^5$ | 2 | 0/10 | 186 |
| SEB Rep | $10^5$ | 3 | 1/20 | n.d. |
| SEB Rep | $10^6$ | 2 | 1/10 | 2785 |
| SEB Rep | $10^6$ | 3 | 4/20 | n.d. |
| SEB Rep | $10^7$ | 2 | 3/10 | 4222 |
| SEB Rep | $10^7$ | 3 | 15/20 | n.d. |
| Challenge controls | | | | Challenge material |
| Lassa N Rep | $10^7$ | 2 | 5/5 | SEB only |
| Lassa N Rep | $10^7$ | 3 | 5/5 | SEB only |
| Lassa N Rep | $10^7$ | 2 | 5/5 | LPS only |
| Lassa N Rep | $10^7$ | 3 | 5/5 | LPS only |

[1]Either micrograms of protein or infectious units of replicon per dose;
[2]inoculations were given 28 days apart; n.d., not determined; GMT, geometric mean titer.

C57BL/6 mice were given 2 or 5 inoculations of mSEA-VRP, 28 days apart, and them challenged 28 days after the last inoculation. The replicon immunized mice failed to produce antibodies and were not protected from an SEA challenge. Swiss mice were given 3 inoculations of mSEA-VRP 28 days apart or 4 inoculations 21 days apart failed to produce antibodies. Right now, we do not understand why the mice are not responding, but plan on conducting another study looking at a prime and boost scheme using a combination of replicon and mSEA/alhydrogel.

What is claimed is:

1. A recombinant DNA construct comprising:

(i) a VEE virus replicon vector which contains (ii) an isolated nucleic acid fragment comprising the nucleic acid sequence encoding mSEA, which sequence expresses a peptide product that does not bind to MHC on T-cells.

2. A recombinant DNA construct according to claim 1 wherein said vector is an expression vector.

3. A recombinant DNA construct according to claim 1, wherein said vector further comprises a prokaryotic vector.

4. An isolated host cell transformed with a recombinant DNA construct according to claim 1.

5. A host cell according to claim 4 wherein said host cell is prokaryotic.

6. A host cell according to claim 4 wherein said host cell is eukaryotic.

7. A method for producing *Staphylococcus aureus* protein comprising culturing the cells according to claim 5 under conditions such that said DNA fragment is expressed and said protein is produced.

8. A method for producing *Staphylococcus aureus* protein comprising culturing the cells according to claim 6 under conditions such that said DNA fragment is expressed and said protein is produced.

9. A recombinant DNA construct comprising:

(i) a VEE virus replicon vector which contains (ii) an isolated nucleic acid fragment comprising the nucleic acid sequence encoding mSEA SEQ ID NO:1.

* * * * *